(12) United States Patent
Topolnjak et al.

(10) Patent No.: US 7,095,823 B2
(45) Date of Patent: Aug. 22, 2006

(54) MULTI-LEAF COLLIMATOR

(75) Inventors: Rajko Topolnjak, Niewuwegein (NL);
Uulke van der Heide, Utrecht (NL);
Jan Lagendijk, Linschoten (NL)

(73) Assignee: Elekta AB (Publ), Stockholm (SE)

( * ) Notice: Subject to any disclaimer, the term of this patent is extended or adjusted under 35 U.S.C. 154(b) by 0 days.

(21) Appl. No.: 10/888,264

(22) Filed: Jul. 7, 2004

(65) Prior Publication Data

US 2005/0008123 A1    Jan. 13, 2005

(30) Foreign Application Priority Data

Jul. 8, 2003    (GB) .................................... 0315909

(51) Int. Cl.
*G21K 1/02*    (2006.01)
(52) U.S. Cl. ...................... 378/152; 378/147
(58) Field of Classification Search ........ 378/147–153, 378/64–65
See application file for complete search history.

(56) References Cited

U.S. PATENT DOCUMENTS

| | | | |
|---|---|---|---|
| 4,882,741 A * | 11/1989 | Brown | 378/152 |
| 4,987,309 A | 1/1991 | Klasen et al. | |
| 5,166,531 A * | 11/1992 | Huntzinger | 250/505.1 |
| 5,748,703 A * | 5/1998 | Cosman | 378/152 |

FOREIGN PATENT DOCUMENTS

EP    0 314 214 A    5/1989

(Continued)

*Primary Examiner*—David V. Bruce
*Assistant Examiner*—Hoon Song
(74) *Attorney, Agent, or Firm*—Kenneth L. Sherman, Esq.; Myers Dawes Andras & Sherman, LLP

(57) ABSTRACT

A multi-leaf collimator is disclosed which alleviates the problems of inter-leaf leakage and pixellation. The collimator comprises a first multi-leaf collimator set, a second multi-leaf collimator set at an acute angle to the first, and a third multi-leaf collimator set at an acute angle to the second. Each multi-leaf collimator set will usually include a pair of leaf banks mutually opposed to each other. The acute angle between the first and the second multi-leaf collimator set is preferably the same as the acute angle between the second and the third set. A suitable angle is about 60°. To improve the penumbra characteristics, (i) the leaves of the multi-leaf collimator closest to the radiation source can be deeper in the direction of the radiation than the leaves of a multi-leaf collimator more distant from the radiation source, (ii) the leaves of the multi-leaf collimator furthest from the radiation source can be shallower in the direction of the radiation than the leaves of a multi-leaf collimator closer to the radiation source, (iii) the tips of the leaves of the multi-leaf collimators can be rounded (iv) the radius of curvature of the tips of the leaves of the multi-leaf collimator closest to the radiation source can be greater than the radius of curvature of the tips of the leaves of a multi-leaf collimator more distant from the radiation source, and (v) the radius of curvature of the tips of the leaves of the multi-leaf collimator furthest from the radiation source can be less than the radius of curvature of the tips of the leaves of a multi-leaf collimator closer to the radiation source. In general, it is also preferred that the first multi-leaf collimator is closest to the radiation source, the third multi-leaf collimator is furthest from the radiation source, and the second multi-leaf collimator is between the first and third multi-leaf collimators.

10 Claims, 5 Drawing Sheets

| FOREIGN PATENT DOCUMENTS | | | WO | WO 99/17305 A | 4/1999 |
|---|---|---|---|---|---|
| JP | 03-009767 | 1/1991 | * cited by examiner | | |

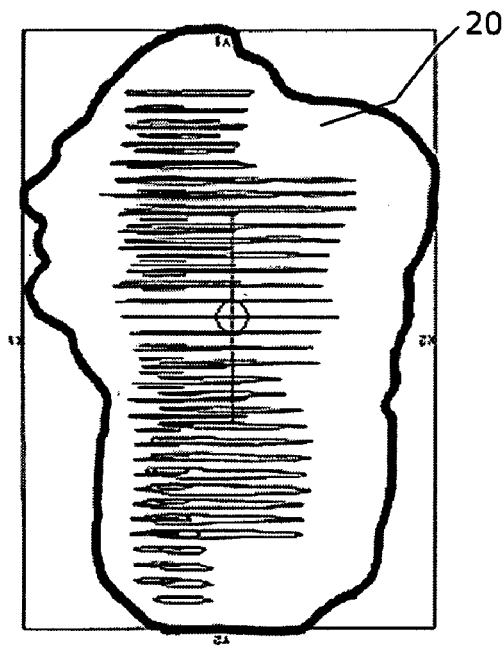
Fig 3
Fig 4 PRIOR ART
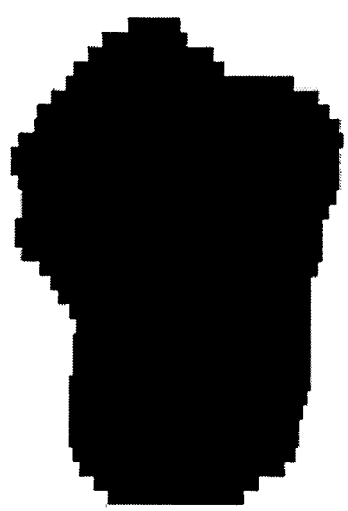
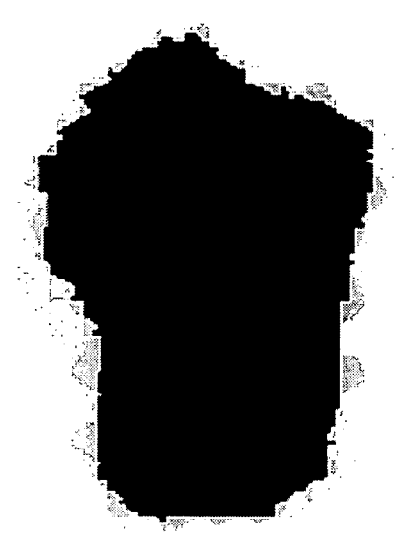
Fig 5 PRIOR ART
Fig 6

MULTI-LEAF COLLIMATOR

FIELD OF THE INVENTION

The present invention relates to a multi-leaf collimator.

BACKGROUND ART

Multi-leaf collimators (MLC) are used (principally) in the field of radiotherapy. A beam of radiation is directed toward a patient and must be collimated to fit the shape of the area to be treated. It is important to ensure that the dose in the areas outside that shape is as low as possible, but also that the whole area is treated. If areas are left untreated then the likelihood of recurrence is increased, whereas if non-treatment regions are irradiated then damage will be caused to healthy tissue resulting in greater side effects and longer recovery times after treatment.

As the treatment area is rarely rectilinear, multi-leaf collimators are employed. These comprise an array of finger-shaped leaves of a radiation-absorbing material, each disposed in a parallel relationship and each able to move longitudinally relative to the others. By moving each leaf to a selected position, a collimator is provided which can exhibit a non-linear edge. In general, one such array (or "bank") will be provided on each side of the beam.

Multi-leaf collimators generally suffer from two difficulties. One is the leakage of radiation between the leaves of the bank, and the other is that the leaves often have square ends and thus exhibit a pixellated pattern when aligned to an edge that is non-perpendicular to the leaf direction.

Various designs are employed to resolve the leakage rate, including stepped edges to the leaves, which therefore interlock (to an extent) and limit the clear view between leaves. However, inter-leaf leakage is a limiting factor in some treatment plans such as Intensity Modulated Radiation Therapy (IMRT) where the treatment time is relatively long.

The pixellation issue is a factor related to the resolution of the leaf bank, and therefore efforts to alleviate this problem tend to involve the use of narrower leaves. This does, however, make the collimator more complex and present significant engineering challenges. JP03009767 suggests the use of two banks of leaves, offset so that the leaves of one cover the gaps between leaves of the other. This results in an improved resolution and reduced leakage, but still gives a pixellated effect.

SUMMARY OF THE INVENTION

The present invention seeks to provide a multi-leaf collimator which further alleviates the problems of inter-leaf leakage and pixellation and provides improved resolution and large field size.

According to a first aspect of the invention there is provided a collimator for a radiation beam comprising a first multi-leaf collimator set, a second multi-leaf collimator set at an acute angle to the first, and a third multi-leaf collimator set at an acute angle to the second.

According to a second aspect of the invention there is provided a collimator for a radiation beam comprising a first multi-leaf collimator set of a certain depth, a second multi-leaf collimator set of a depth which is less than the depth of the first set and set at an acute angle to the first, and a third multi-leaf collimator set of a depth which is less that the depth of the second set and which is set at an acute angle to the second.

Each multi-leaf collimator set will usually include a pair of leaf banks mutually opposed to each other.

The acute angle between the first and the second multi-leaf collimator set is preferably the same as the acute angle between the second and the third set. A suitable angle is approximately 60°, however other suitable angles may also be used.

The penumbra is the region close to the radiation field edge. The penumbral width is typically defined by the distance between the points where 20% and 80% of the dose at central axis is delivered. A small penumbra means a good beam definition which allows to give maximum dose to a target volume with a rapid dose fall off next to it towards the surrounding normal healthy tissue.

A number of design features in such a collimator are preferred in order to improve the penumbra characteristics:

The leaves of the multi-leaf collimator closest to the radiation source can be deeper in the direction of the radiation than the leaves of a multi-leaf collimator more distant from the radiation source.

The leaves of the multi-leaf collimator furthest from the radiation source can be shallower in the direction of the radiation than the leaves of a multi-leaf collimator closer to the radiation source.

The tips of the leaves of the multi-leaf collimators can be rounded.

The radius of curvature of the tips of the leaves of the multi-leaf collimator closest to the radiation source can be greater than the radius of curvature of the tips of the leaves of a multi-leaf collimator more distant from the radiation source.

The radius of curvature of the tips of the leaves of the multi-leaf collimator furthest from the radiation source can be less than the radius of curvature of the tips of the leaves of a multi-leaf collimator closer to the radiation source.

In general, it is also preferred that the first multi-leaf collimator is closest to the radiation source, the third multi-leaf collimator is furthest from the radiation source, and the second multi-leaf collimator is between the first and third multi-leaf collimators.

BRIEF DESCRIPTION OF THE DRAWINGS

An embodiment of the present invention will now be described by way of example, with reference to the accompanying figures in which;

FIG. 3 shows a typical clinical example;

FIG. 4 shows the achieved irradiation pattern using a two-bank multi-leaf collimator with 10 mm leaves;

FIG. 5 shows the achieved irradiation pattern using a two-bank multi-leaf collimator with 4 mm leaves;

FIG. 6 shows the achieved irradiation pattern using a three bank multi-leaf collimator according to the present invention with 10 mm leaves;

DETAILED DESCRIPTION OF THE EMBODIMENTS

Figure 1:
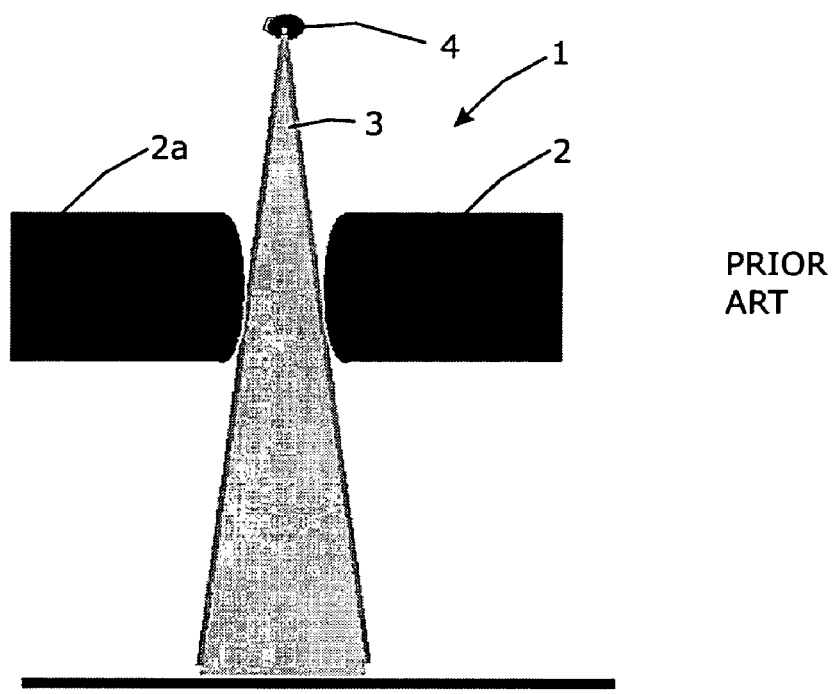
FIG. 1 shows a known single bank multi-leaf collimator in vertical section.

FIG. 1 shows the relevant part of a beam collimator 1 of conventional design. The collimator 1 comprises a set of a pair of multi-leaf banks 2, 2a disposed in a plane orthogonal to the direction of the X-ray or other beam 3 exiting from the aperture 4.

Figure 2:
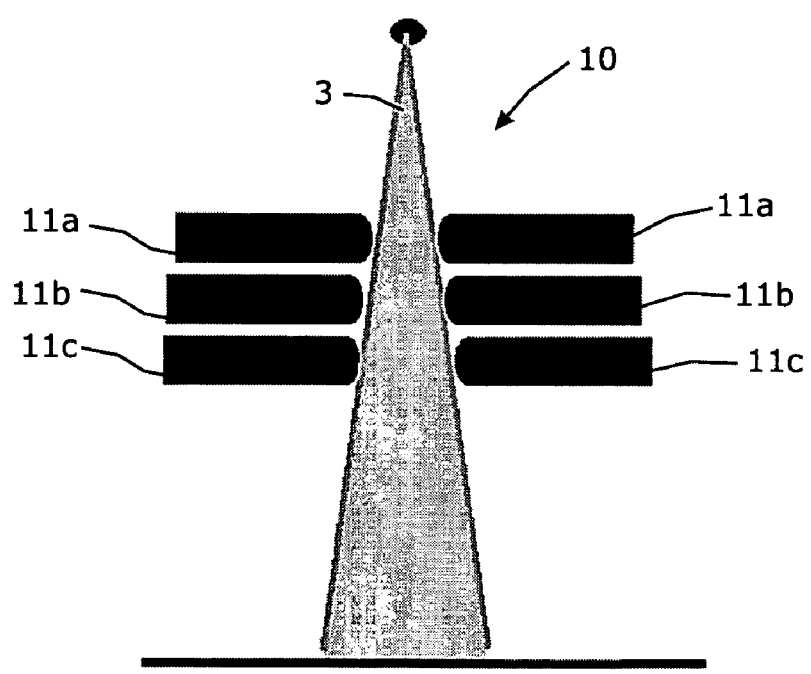
FIG. 2 shows a multi-leaf collimator according to the present invention in a corresponding vertical section.

FIG. 2 shows the collimator 10 according to the present invention, in a corresponding vertical plane (i.e. in the direction of the beam 3) to FIG. 1 of the conventional type of collimator. The collimator comprises three multi-leaf sets, 11a, 11b and 11c, each set comprising a multi-leaf bank disposed on either side of the X-ray beam 3, and each disposed in a row in the vertical section. What is not visible in FIG. 2 is that the three banks are arranged in different orientations, such as with their leaf direction at 60° to each other.

Figure 10:
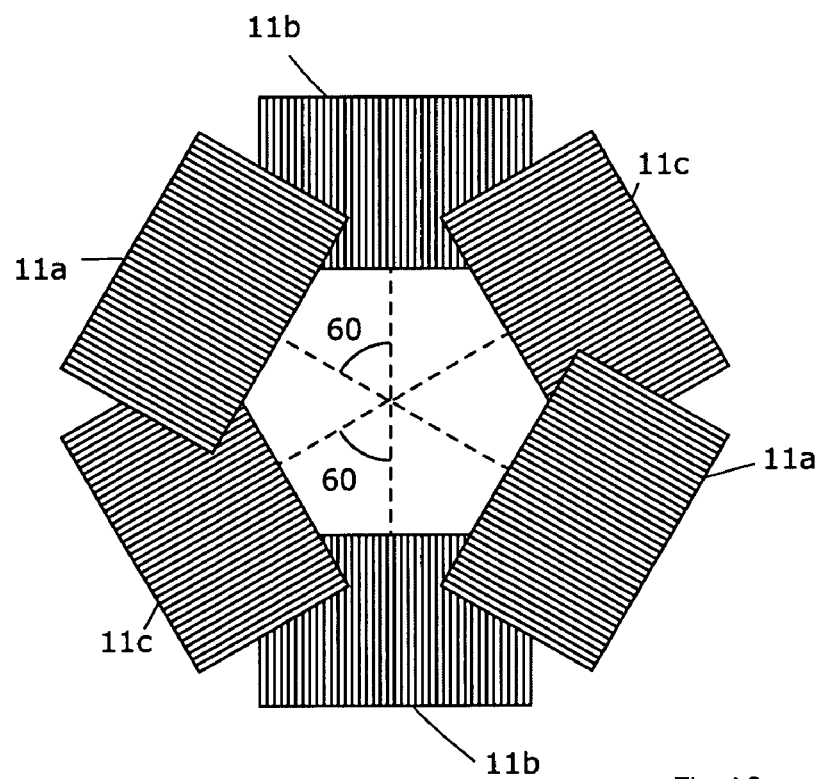
FIG. 10 shows a top view of the multi-leaf collimator of FIG. 2, illustrating an example of acute angles between the collimator multi-leaf sets in FIG. 2.

FIG. 10 shows a top view of the multi-leaf collimator 10 of FIG. 2, wherein FIG. 10 illustrates an example of acute angles of 60 degrees between leaf directions of the sets 11a, 11b and between leaf directions of the sets 11b and 11c.

FIG. 3 shows a typical clinical sample 20 with an irregular, rectilinear shape, which is to be treated using treatment plans such as IMRT. The area inside the solid black line forming the perimeter of the shape is the tissue which must be treated with X-rays or other radiation. In order that the tissue surrounding the treatment area, i.e. the healthy tissue, is not affected, the area to be treated must receive the radiation treatment whilst the healthy tissue must be shielded from the radiation using suitable radiation-blocking material.

FIG. 4 shows the achieved irradiation pattern using a two-bank multi-leaf collimator such as the conventional type shown in JP03009767. The width of the leaves in this particular example are of 10 mm. The width of the leaves is measured in the plane orthogonal to the direction of the beam. As can be seen, large areas of healthy tissue will be irradiated due to the approximate boundary that is achieved using the conventional two-bank multi-leaf collimator.

If the width of the leaves is decreased, i.e. to achieve a better resolution, in this example to 4 mm to produce a mini-collimator, the resulting irradiation pattern is closer to the pattern of the tissue to be treated, as shown in FIG. 5. Of course, the narrower the leaves of the bank, the better the resolution, however, the leaves of the bank can only be narrowed to a finite width as engineering challenges become insurmountable. Furthermore, the narrower the leaves of the bank, the smaller becomes the practically achievable field size, thus making it difficult to treat large areas.

The field size of the conventional two bank multi-leaf collimator is of the order of 40×40 cm$^2$. The field size of the mini-collimator is of the order of 16×20 cm$^2$. The field size of the collimator according to the present invention, however, is at least 40 cm diameter, and may be greater.

FIG. 6 shows the achieved irradiation pattern using a collimator according to the present invention, with 10 mm wide leaves. As can be seen the target irradiation pattern is improved substantially over that achieved by using either the 10 mm width leaves of the conventional two-bank multi-leaf collimator or the narrower leaves of the mini-collimator used to achieve the pattern in FIG. 5.

Figure 7:
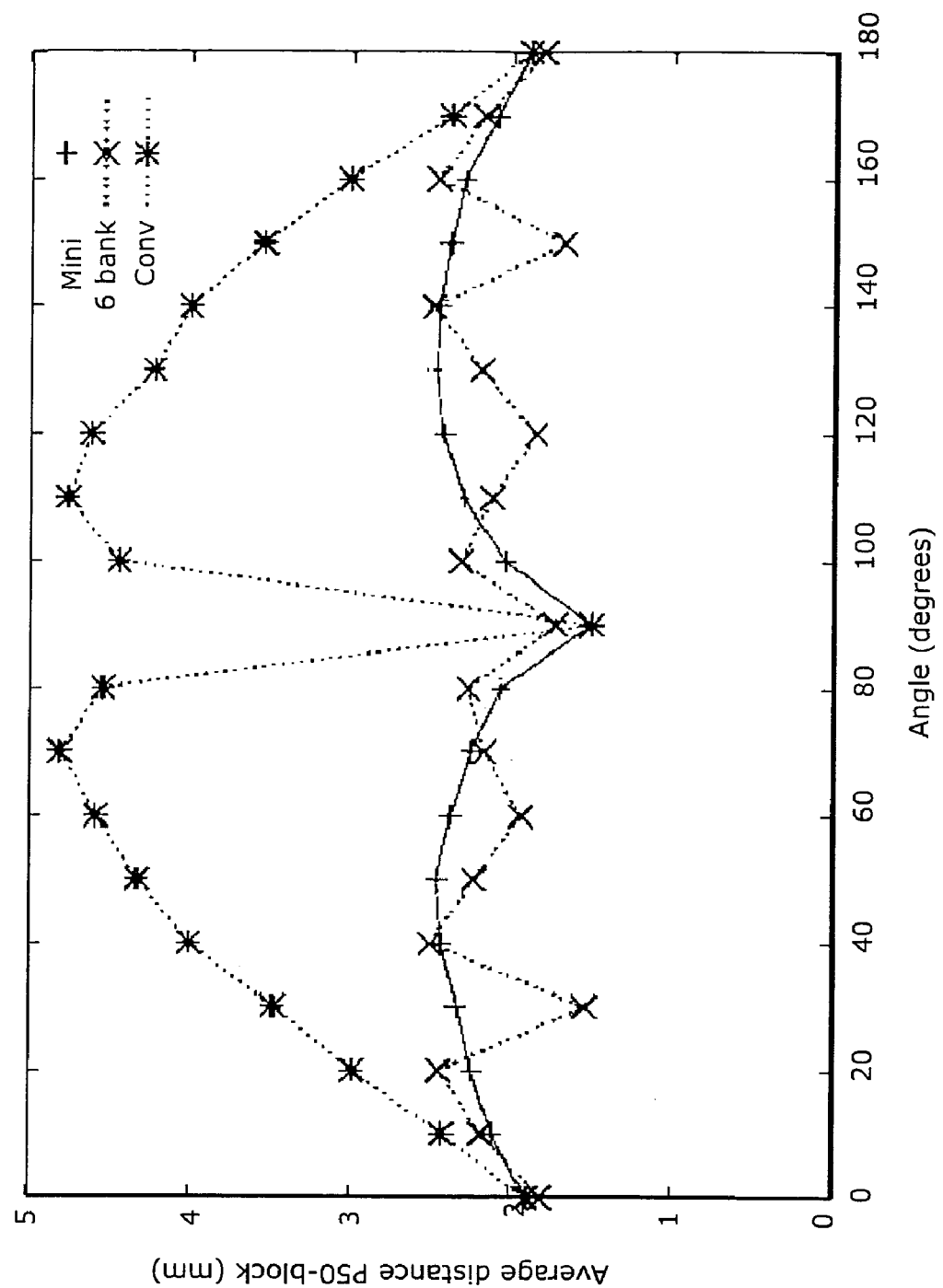
FIG. 7 shows the overdose applied for a standard target at a range of orientations.

FIG. 7 shows the overdose, i.e. irradiation of healthy tissue, applied for a standard target and range of orientations. As can be seen, using the conventional two-bank collimator, the overdose is minimum in only two orientations, i.e. when the area to be treated has a vertical or horizontal edge and thus the leaves of the conventional collimator may be placed in a close abutting relationship with the edge. The same is true of the mini-collimator, where again the overdose forms minima at two orientations. The results of the collimator according to the present invention, show a marked and substantial improvement in the reduction of the overdose, as can be seen from the graph, most of the overdose line lies well below the line achieved using the mini-collimator.

Figure 8:
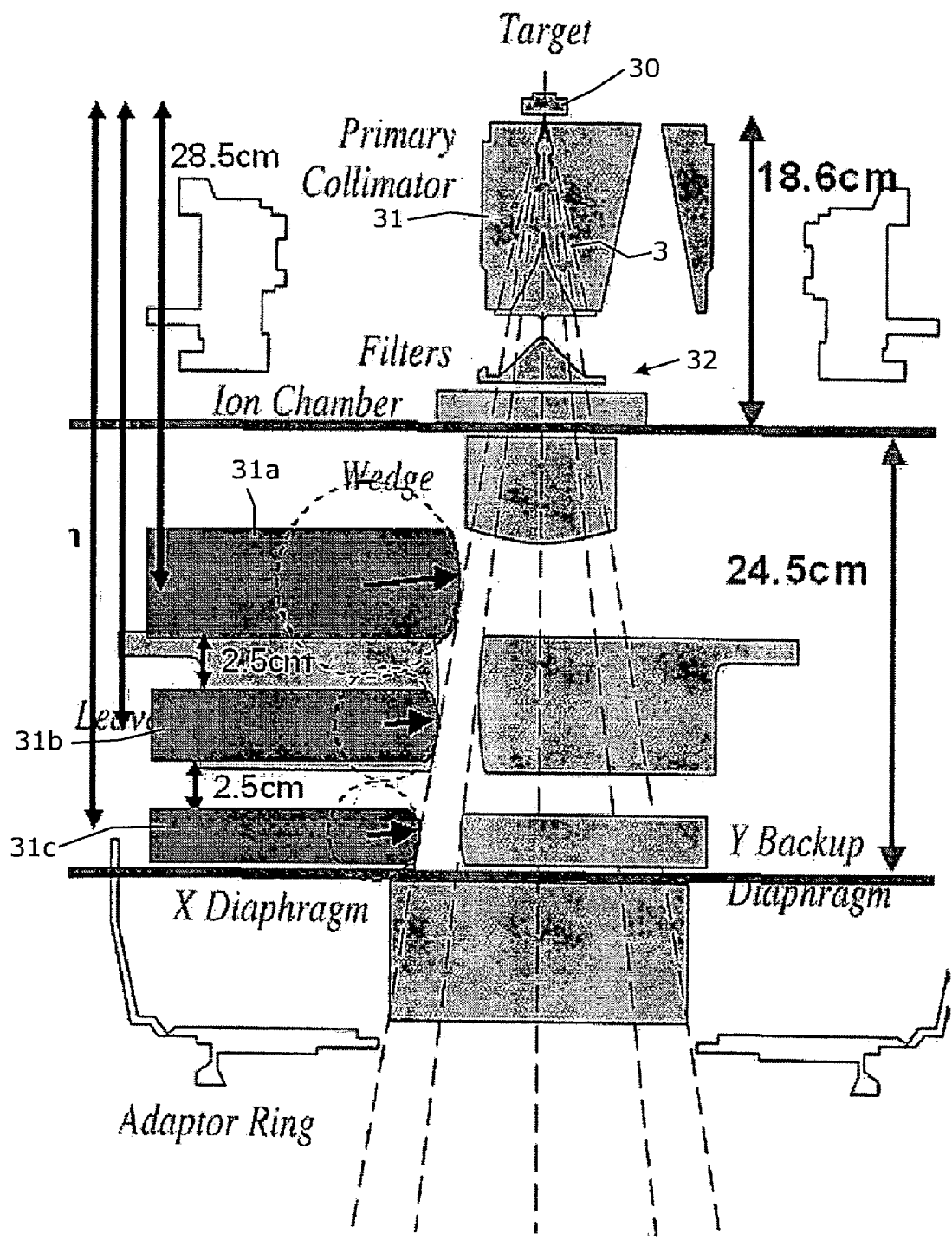
FIG. 8 shows a vertical section through an accelerator partially fitted with a multi-leaf collimator according to the second aspect of the invention.

FIG. 8 shows the embodiment according to a second aspect of the invention. The multi-leaf collimator set is shown partially fitted into an accelerator. The accelerator comprises a target to generate the radiation, a primary collimator 31 which partially collimates the beam 3, and filters 32 to filter the beam. The beam then passes through the multi-leaf collimator according to a second aspect of the invention. The depth of the leaves is measured in a direction parallel to the direction of the X-ray beam 3. The depth of the bank of leaves 31a is the greatest, the depth of the second bank 31b is less than the depth of the first bank of leaves and the depth of bank of leaves 31c is less than the depth of the second bank of leaves.

The leaves are also curved in the direction parallel to the direction of the beam, with the radius of curvature of the first bank of leaves 31a being greater than the radius of curvature of the second bank of leaves 31b. The radius of curvature of the third bank of leaves 31c, is smaller than the radius of curvature of the second bank of leaves.

Figure 9:
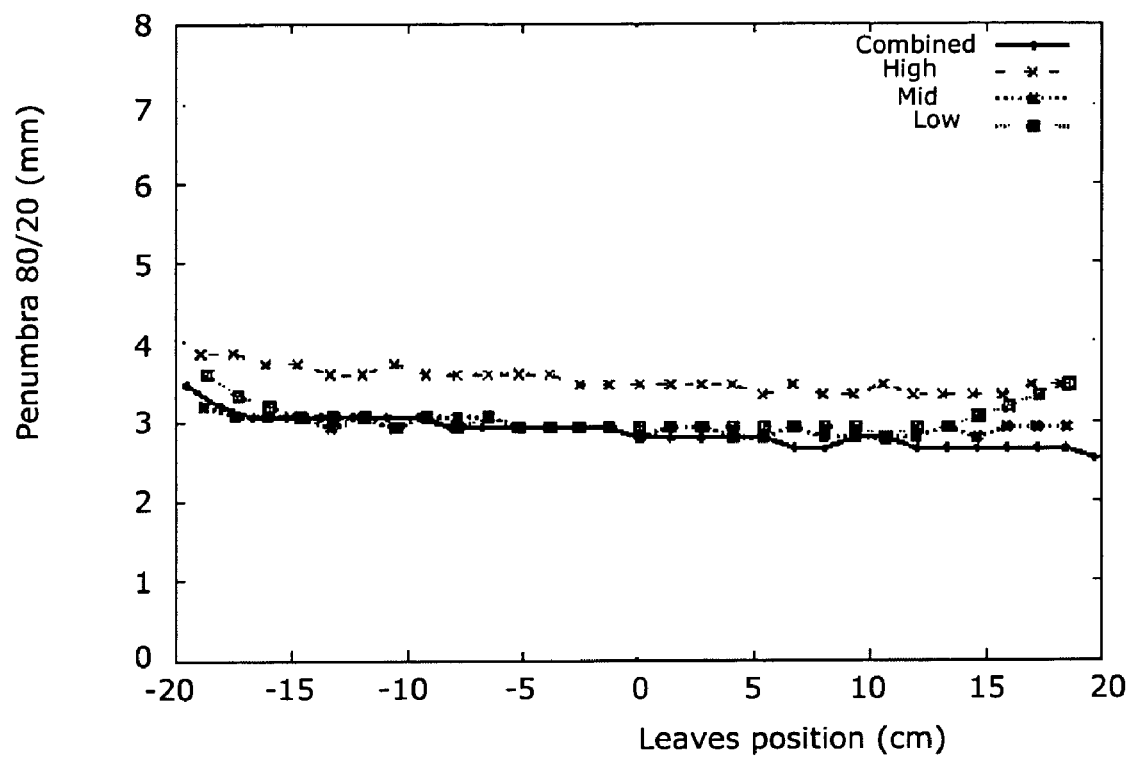
FIG. 9 shows the penumbra profile achieved by the multi-leaf collimator of FIG. 8.

FIG. 9 shows the resulting penumbra for this second aspect of the invention, which is improved almost two-fold compared with the conventional two-bank collimator. The percentage of the area outside of the collimator pattern that receives between 20–100% of the radiation for a conventional two-bank collimator is typically of the order of 13%. For the mini-collimator this is reduced to around 8%, but the multi-bank collimator according to the present invention, achieves a fluency of around 7%.

Therefore, it can be seen that the multi-bank multi-leaf collimator of the present invention includes the advantages of the large two-bank conventional collimator in terms of the field size and yet has the fluency, resolution and performance of the mini-collimator.

In addition, the use of a collimator according to the present invention allows the design of MLC heads that are significantly simpler. The leaves need not employ tongue and groove mechanisms at their joint, as other banks of leaves above and/or below can cover these joins. Furthermore, the collimator head does not need to be rotateable as the collimator is less directional.

It will of course be understood that many variations may be made to the above-described embodiment without departing from the scope of the present invention.

The invention claimed is:

1. A collimator for a radiation beam comprising:
   a first multi-leaf collimator set;
   a second multi-leaf collimator set at an acute angle to the first multi-leaf collimator set; and
   a third multi-leaf collimator set at an acute angle to the second multi-leaf collimator set.

2. A collimator according to claim 1 in which each multi-leaf collimator set includes a pair of leaf banks mutually opposed to each other.

3. A collimator according to claim 1 in which the acute angle between the first and the second multi-leaf collimator set is the same as the acute angle between the second and the third set.

4. A collimator according to claim 1 in which at least one of the acute angles is 60°.

5. A collimator according to claim 1 in which the leaves of the multi-leaf collimator closest to the radiation source are deeper in the direction of the radiation than the leaves of a multi-leaf collimator more distant from the radiation source.

6. A collimator according to claim 1 in which the leaves of the multi-leaf collimator furthest from the radiation source are shallower in the direction of the radiation than the leaves of a multi-leaf collimator closer to the radiation source.

7. A collimator according to claim 1 in which the tips of the leaves of the multi-leaf collimators are rounded.

8. A collimator according to claim 7 in which the radius of curvature of the tips of the leaves of the multi-leaf collimator closest to the radiation source is greater than the radius of curvature of the tips of the leaves of a multi-leaf collimator more distant from the radiation source.

9. A collimator according to claim 7 in which the radius of curvature of the tips of the leaves of the multi-leaf collimator furthest from the radiation source is less than the radius of curvature of the tips of the leaves of a multi-leaf collimator closer to the radiation source.

10. A collimator according to claim 1, in which the first multi-leaf collimator is closest to the radiation source, the third multi-leaf collimator is furthest from the radiation source, and the second multi-leaf collimator is between the first and third multi-leaf collimators.

* * * * *